(12) United States Patent
De Scheerder et al.

(10) Patent No.: US 6,572,651 B1
(45) Date of Patent: Jun. 3, 2003

(54) STENTS WITH A DIAMOND LIKE COATING

(75) Inventors: Ivan De Scheerder, Sint-Martens-Latem (BE); Eddy Demeyere, Marke (BE); Dominique Neerinck, Hertsberge (BE); Wilfried Coppens, Marke (BE)

(73) Assignee: N.V. Bekaert S.A., Zwevegem (BE)

( * ) Notice: Subject to any disclaimer, the term of this patent is extended or adjusted under 35 U.S.C. 154(b) by 0 days.

(21) Appl. No.: 09/701,393

(22) PCT Filed: Apr. 27, 1999

(86) PCT No.: PCT/EP99/03022

§ 371 (c)(1),
(2), (4) Date: Jan. 11, 2001

(87) PCT Pub. No.: WO99/62572

PCT Pub. Date: Dec. 9, 1999

(30) Foreign Application Priority Data

Jun. 3, 1998 (EP) .............................. 98201835

(51) Int. Cl.$^7$ .................................. A61F 2/06
(52) U.S. Cl. ...................... 623/1.44; 623/1.15
(58) Field of Search ............... 623/1.15, 1.43, 623/1.44, 1.46

(56) References Cited

U.S. PATENT DOCUMENTS

| | | | |
|---|---|---|---|
| 4,739,762 A | 4/1988 | Palmaz | 128/343 |
| 4,856,516 A | 8/1989 | Hillstead | 128/343 |
| 5,133,732 A | 7/1992 | Wiktor | 606/195 |
| 5,135,536 A | 8/1992 | Hillstead | 606/195 |
| 5,158,548 A | 10/1992 | Lau et al. | 604/96 |
| 5,161,547 A | 11/1992 | Tower | 238/898 |
| 5,163,958 A | 11/1992 | Pinchuk | 623/11 |
| 5,183,085 A | 2/1993 | Timmermans | 140/89 |
| 5,282,825 A | 2/1994 | Muck et al. | 606/203 |
| 5,352,493 A | 10/1994 | Dorfman et al. | 427/530 |
| 5,647,858 A | 7/1997 | Davidson | 604/264 |
| 5,690,670 A | * 11/1997 | Davidson | 606/198 |

FOREIGN PATENT DOCUMENTS

| | | |
|---|---|---|
| EP | 0 382 014 B1 | 8/1990 |
| EP | 0 282 175 B1 | 11/1991 |
| EP | 0 540 290 A2 | 5/1993 |
| EP | 2 128 637 A | 5/1994 |
| EP | 0 615 769 A1 | 9/1994 |
| EP | 0 621 017 A1 | 10/1994 |
| EP | 0 657 147 A2 | 6/1995 |
| EP | 0 662 307 A1 | 7/1995 |
| EP | 0 669 114 A1 | 8/1995 |
| EP | 0 791 341 A1 | 8/1997 |
| GB | 2 287 473 A | 9/1995 |
| WO | WO 94/17754 | 8/1994 |
| WO | WO 96/39943 | 12/1996 |
| WO | WO 97/40207 | 10/1997 |
| WO | WO 98/33948 | 1/1998 |

OTHER PUBLICATIONS

Chandra L, et al., "The Effect of Biological Fluids on the Adhesion of Diamond–like Carbon Films to Metallic Substrates", Diamond and Related Materials, vol. 4, No. 5/06, May 1, 1995, pp. 852–856.

Olborska A, et al., "Amorphous carbon–biomaterial for implant coatings", Diamond and Related Materials, vol. 3, No. 4/06 Apr. 1, 1994, pp. 899–901.

Mitura E, et al., "Diamond–like Carbon Coatings for biomedical applications", Diamond and Related Materials, vol. 3, No. 4/06, Apr. 1, 1994, pp. 896–898.

* cited by examiner

Primary Examiner—Bruce Snow
(74) Attorney, Agent, or Firm—Foley & Lardner

(57) ABSTRACT

An intravascular metal stent having a tubular wall and a biocompatible coating on at least a major part of the wall surface which coating has a thickness of less than 4 μm and contains a diamond like amorphous material, preferably DLN.

14 Claims, 1 Drawing Sheet

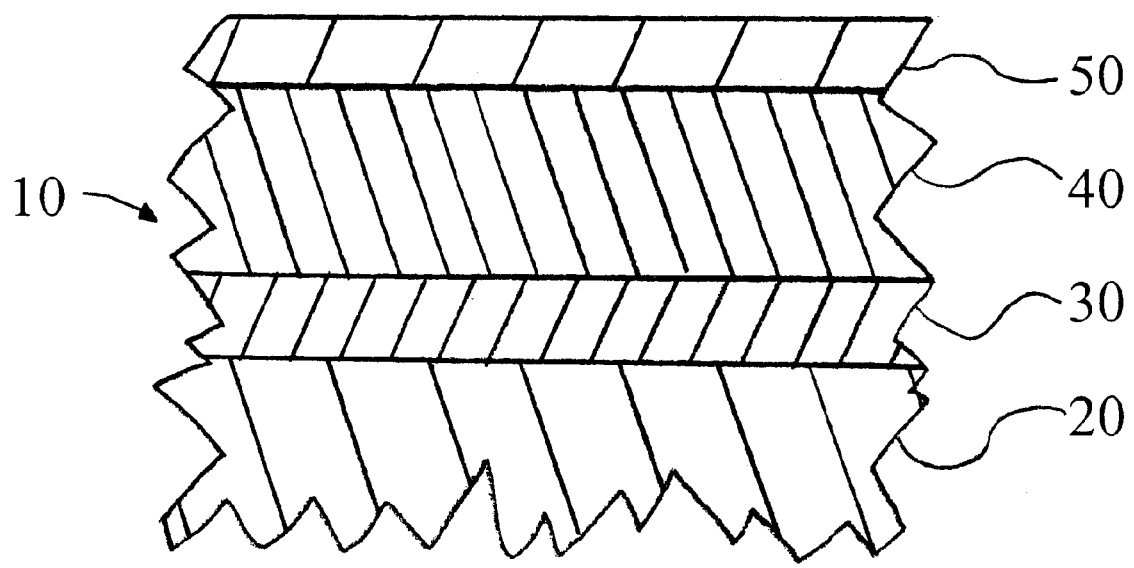

STENTS WITH A DIAMOND LIKE COATING

FIELD OF THE INVENTION

The present invention relates to an intravascular stent which is coated with a specific biocompatible composition.

BACKGROUND OF THE INVENTION

It is known that heparin, phosphorylcholine and certain polymer coatings may decrease the thrombogenicity of coronary stents. However they do not appear to reduce neointimal hyperplasia and in-stent restenosis. A large variety of vasoactive substances can easily be embedded in the polymer network without firm chemical bonds. Consequently they potentially can act as an intramural slow release formulation for vasoactive drugs.

Numerous tubular stent designs are now on the market. Many of them consist of a radially expandable metal network, either in the form of a fine wire mesh, of a corrugated ring structure or of a slotted metal tube wall wherein a recurring pattern of holes are cut (e.g. by laser cuting). The stent wall has a thickness of between 0.08 and 0.20 mm and the metal is preferably stainless steel, tantalum or NITINOL. Stents can also have an expandable tubular metal spring like structure (coil stent). Examples of stent structures are known from e.g. U.S. Pat. Nos. 4,739,762, 4,856,516, 5,133,732, 5,135,536, 5,161,547, 5,158,548, 5,183,085, 5,282,823, from WO 94/17754, from European patent applications Nos. 0282175, 0382014, 0540290, 0621017, 0615769, 0669114, 0662307, 0657147 and from European patent application 0791341 of applicant.

Diamond like amorphous material such as diamond like nano composition (DLN) are known from WO97/40207 and WO98/33948.

The use of DLN as biocompatible coating for medical devices is for example known from U.S. Pat. No. 5,352,493, WO 97/40207 and WO 96/39943. U.S. Pat. No. 5,352,493 and WO96/39943 disclose the application of DLN as biocompatible coating for medical devices such as orthopedic devices. WO 97/40207 describes the application of DLN for coating of hip prostheses. In contrast with the above mentioned applications, the coating of intravascular implants, such as stents must meet more severe requirements. The coating needs not only to meet the requirement to be biocompatible, but has to decrease or even to avoid thrombogenicity and histiolymphocytic inflammatory foreign body reaction. Neointimal hyperplasia has to be avoided since it can result in a narrowing or even in a closing of the blood vessel cavity. The narrowing of the blood vessel cavity after implantation of a stent is known as in-stent restenosis.

SUMMARY OF THE INVENTION

It is an object of the present invention to provide an intravascular stent coated with a biocompatible material in order to avoid thrombogenicity, histiolympocytic inflammatory foreign body reaction and neointimal hyperplasia. As a consequence the risk for in-stent restenosis is decreased or avoided.

The object of the invention is met by using a new class of biocompatible materials for coating at least a major part of the wall surface of the stent with a coating thickness of preferably less than 4 μm and most preferably between 0.05 and 3 μm. The material used according to the invention contains a diamond like amorphous material. Since the coating resists repeated deformation, it can be applied to a stent with a radially expandable metal mesh or metal coil structure.

The diamond like amorphous material in the coating is preferably a diamond like nano composition (DLN) comprising interpenetrating networks of a-C:H and a-Si:O. Such coatings and methods to apply them are known i.a. from WO 97/40207, PCT/EP97/01878 and WO98/33948. A representative coating of a-C:H and a-Si:O comprises 30 to 70 at % of C, 20 to 40 at % of H, 5 to 15 at % of Si and 5 to 15% of O. For applying these coatings to stents, the latter are preferably in their expanded state, not only radially but also they are longitudinally (axially) stretched to a certain extent if the mesh or spring structure so permits. This allows a substantially uniform deposition of the biocompatible diamond like material (DLN) using plasma-assisted CVD-processes. The plasma is created from a siloxane precursor. A Si-doped DLC can also be deposited; a silane precursor is then used.

BRIEF DESCRIPTION OF THE DRAWINGS

The drawing shows a cross-sectional view of an embodiment of the present invention.

DESCRIPTION OF THE PREFERRED EMBODIMENTS OF THE INVENTION

The invention will now be illustrated by the description of two exemplary embodiments. The coronary stent of a coil-type design was used, as described in U.S. Pat. No. 5,183,085. It consisted of a preconditioned, non ferromagnetic, highly polished stainless steel wire (AISI 316L) with a diameter of 0.18 mm. This design allows folding (radial compression) on any conventional balloon, resulting in a low profile 6F guiding catheter compatible stent delivery system. Percentage of axial shortening upon expanding the balloon is less than 5% and the stent is available in lengths from 12 mm up to 40 mm allowing customized stenting. These stents are available as bare stents or as mounted stents. In the present example stents of a length of 16 mm were used. Highly polished laser cut stainless steel mesh stents can be used as well.

The coil stent in its radially expanded form (as shown FIG. 1 of U.S. Pat. No. 5,183,085) was mounted as cathode in the vacuum reactor where the diamond like nanocomposition was deposited.

In a first embodiment, a single diamond like nanocomposition material (DLN) of the type described in claim 2 of WO 97/40207 was deposited with an average thickness of 2.5 μm. In a second embodiment a coating with the same thickness was deposited, using essential features of the process of WO 98/33948. That is, referring to the drawing, a stent (10) was formed by depositing a first layer (30) of the diamond like nanocomposite material on a wall (20) with an average thickness of 0.5 μm. On top of that, a layer (50) of the same average thickness of diamond like carbon (DLC= a-C:H) was deposited with a transition layer (40) in between having a thickness of 1.5 μm and comprising a mixture with a composition changing gradually from the first nanocomposition (DLN) to the DLC. The coating on the outer side of the coil was generally slightly thicker than on its inner side. The outer surface of the coated wire of the stent was extremely even and smooth.

Both embodiments were subjected to cyclic fatigue bending tests to determine their adhesion behaviour and adhesion retention to the wire after a number of bending cycles. No significant separation of the coating from the steel surface was discovered, especially for the stent with the single DLN-coating since indeed the critical load in a scratch test had indicated before a value of 33 to 36 N. The scratch tests were perfomed at about 50% relative humidity at 22° C. with a Revetest device (CSEM). The scratch stylus used is a diamond Rockwell C tip (120° C. on with a 200 $\mu$m tip radius). The loading rate is 100 N/mm, whereas the displacement rate of the stylus on the coating is 10 mm per minute. The critical load is determined with optical microscopy and corresponds to the load where delamination of the coating starts at the edges of the scratch track. It is thus confirmed here that DLN offers an excellent adhesion and adhesion retention after repeated bending. The inert diamond like material presents at the same time a suitable protective layer against possible corrosive attack of the steel surface (release of Cr, Ni and/or Fe) by the blood and vascular tissue in contact with the stent surface.

The stents were then radially compressed on a balloon catheter (diameter 3 to 3.5 mm) to the configuration shown in FIG. 3 of U.S. Pat. No. 5,183,085 and randomly implanted in a series of coronary arteries of 20 domestic cross bred pigs of both sexes weighing 25 to 30 kg. Thirteen specimen of each of three types of stents, viz. coated stents according to the first and to the second embodiment described above and (as third type) non coated, highly polished stainless steel spring stents were implanted for comparison. All stent deployments and implantations were successful and resulted in properly stented vessel segments. The pigs were fed throughout the study period with a standard natural grain diet without lipid or cholesterol supplementation. All animals were treated and cared for in accordance with the National Institute of Health Guide for the Care and, Use of Laboratory Animals. Six weeks after implantation, control angiography of the stented vessels was performed and subsequently pigs were sacrificed. At that time their average weight was about 70 kg and the vessels had thus grown considerably, compared to their size at the time of implantation.

Angiographic analysis (quantitative coronary angiography) of stented vessel segments was performed before stenting, immediately after stenting, and at follow-up using the POLYTRON 1000-system as described by De Scheerder et al. in the Journal of Invasive Cardiology 1996; 8: 215–222. The lumen diameters of the vessel segments were measured before stent implantation (=pre-stenting artery diameter values), immediately thereafter (=post-stenting values) and at follow-up (=diameters after 6 weeks). The degree of oversizing (%) was expressed as measured maximum balloon size minus selected artery diameter divided by the selected artery diameter. Recoil (%) was expressed as measured maximum balloon size minus mimimal stent lumen diameter (measured 15 minutes after stent implantation) and divided by measured maximum balloon size. The late loss value is an indication of hyperplasia and is the difference between the post-stenting value and the diameter at follow-up. The results of the angiographic measurements for each of the three types of stents is summarized in table 1.

TABLE 1

| Mean Artery diameter (mm) | Non-coated | Coating DLN | Coating DLN/DLC |
| --- | --- | --- | --- |
| Pre-stenting (mm) | 2.52 ± 0.18 | 2.57 ± 0.22 | 2.41 ± 0.18 |
| Balloon size (mm) | 2.93 ± 0.16 | 2.96 ± 0.10 | 2.91 ± 0.15 |
| Post-stenting (mm) | 2.68 ± 0.16 | 2.71 ± 0.20 | 2.64 ± 0.14 |

TABLE 1-continued

| Mean Artery diameter (mm) | Non-coated | Coating DLN | Coating DLN/DLC |
| --- | --- | --- | --- |
| Oversizing (%) | 16 ± 6 | 16 ± 8 | 21 ± 7 |
| Recoil (%) | 8 ± 4 | 8 ± 4 | 9 ± 6 |
| 6 weeks FU (mm) | 2.52 ± 0.29 | 2.65 ± 0.27 | 2.54 ± 0.37 |
| Late loss | 0.16 ± 0.28 | 0.06 ± 0.27 | 0.10 ± 0.34 |

Baseline selected arteries, measured balloon diameter and post stenting diameter were similar for the three types. Oversizing and recoil were also similar. At six week follow-up a somewhat larger minimal luminal stent diameter and a somewhat decreased late loss was found for the DLN-coated stent embodiment.

After the pigs were sacrificed coronary segments were carefully dissected together with 10 mm minimum vessel segment both proximal and distal to the stent. Histopathology, as evaluated by light microscopic examination, was performed on very thin cross-section slices of the stented artery sections. Injury of the arterial wall, due to stent deployment, was evaluated as a first factor and graded according to the method of Schwartz et al. (J.Am. Coll. Cardiol 1992; 19: 267–274). Likewise, inflammatory reaction at every stent filament site was examined (second factor) by searching for inflammatory cells and graded as well. Appearance of thrombus was evaluated as a third factor and graded. The mean value of every factor for the 12 samples of each of the three stent types was calculated.

Thrombus formation was decreased in both coated stent types, i.e. with coatings DLN, resp. DLN/DLC. However, histopathology revealed for the non-coated stents and for the DLN/DLC-coated stents an increased inflammatory reaction when compared to the stent type with the single DLN-coating. It is believed that the inert DLN-coating is particularly useful to retard the attraction and sticking of proteins to the stent surface.

Finally, a morphometric study was carried out on the stented vessel segments at the time of follow-up after six weeks of implantation. The study was made using a computerized morphometry program (Leitz CBA 8000). Measurements of lumen area, lumen inside the internal elastic lamina area (=IEL area) and lumen inside the external elastic lamina area (=EEL area) were performed on the arterial sites, all in $mm^2$. Neointimal hyperplasia (=IEL area minus Lumen area) and area stenosis in % as the ratio of hyperplasia to IEL area were derived therefrom. The results are shown in table 2.

TABLE 2

| Mean Cross Section Area ($mm^2$) | Non-coated | Coating DLN | Coating DLN/DLC |
| --- | --- | --- | --- |
| Lumen area ($mm^2$) | 1.71 ± 0.66 | 2.31 ± 0.89 | 1.93 ± 0.73 |
| IEL area ($mm^2$) | 3.87 ± 1.39 | 3.84 ± 0.67 | 3.59 ± 0.54 |
| EEL area ($mm^2$) | 5.74 ± 2.06 | 5.15 ± 0.89 | 4.95 ± 0.66 |
| Hyperplasia ($mm^2$) | 2.16 ± 1.48 | 1.53 ± 0.54 | 1.66 ± 0.38 |
| Area stenosis (%) | 54 ± 15 | 41 ± 17 | 48 ± 16 |

Again the DLN-coated stents offered the best results, i.e. the largest lumen area after 6 weeks, caused by a decreased neointimal hyperplasia. Covering the DLN/DLC- or DLN-coated stents with a heparin or phosphorycholine layer may further decrease neointimal hyperplasia.

Although the invention has been described for blood vessels, similar results can be obtained for stents with diamond like coatings in other vessels in animal and human bodies, such as life stream conducts.

What is claimed is:

1. An intravascular stent having a tubular wall and a biocompatible coating on at least a major part of the wall surface, said coating having a thickness of less than 4 µm and containing closest to the wall a diamond like nanocomposite (DLN) material, said nanocomposite material comprising two interpenetrating networks of a-C:H and a-Si:O and wherein said material is covered with a transition layer comprising a mixture of said nanocomposite material (DLN) and a diamond like carbon (DLC), and further with a DLC layer.

2. A stent according to claim 1 wherein the stent wall is a radially expandable metal mesh or metal spring structure.

3. A stent according to claim 2 wherein the metal structure is a polished stainless steel structure.

4. A stent according to claim 1 wherein the material comprises 30 to 70 at % of C, 20 to 40 at % of H, 5 to 15 at % of Si and 5 to 15% of O.

5. The intravascular stent of claim 1, wherein the transition layer is located between the DLN material and the DLC layer.

6. The intravascular stent of claim 1, wherein the mixture of the transition layer changes gradually from DLN to DLC.

7. The intravascular stent of claim 6, wherein the change of the mixture of the transition layer from DLN to DLC is correlated to an increase in distance from the stent.

8. The intravascular stent of claim 1, wherein the DLN material closest to the wall has a thickness of about 0.5 µm.

9. The intravascular stent of claim 1, wherein the transition layer has a thickness of about 1.5 µm.

10. The intravascular stent of claim 1, wherein the DLC has a wall thickness greater than about 0.5 µm.

11. The intravascular stent of claim 1, wherein the DLN material closest to the wall has a thickness of about 0.5 µm, wherein the transition layer has a thickness of about 1.5 µm, and wherein the DLC has a wall thickness of about 0.5 µm, the combined thickness of the three layers being less than 4 µm.

12. The intravascular stent of claim 11, wherein the transition layer is located between the DLN material and the DLC layer.

13. The intravascular stent of claim 12, wherein the mixture of the transition layer changes gradually from DLN to DLC.

14. The intravascular stent of claim 13, wherein the change of the mixture of the transition layer from DLN to DLC is correlated to an increase in distance from the stent.

* * * * *